(12) United States Patent
Brading et al.

(10) Patent No.: US 8,916,139 B2
(45) Date of Patent: Dec. 23, 2014

(54) ORAL CARE COMPOSITIONS

(75) Inventors: Melanie Gayle Brading, Wirral (GB); Stephen Golding, Wirral (GB); Alison Katharine Green, Wirral (GB); David Thomas Littlewood, Wirral (GB); Ann Elizabeth Scott, Wirral (GB)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 13/638,936

(22) PCT Filed: Apr. 5, 2011

(86) PCT No.: PCT/EP2011/055278
§ 371 (c)(1),
(2), (4) Date: Oct. 17, 2012

(87) PCT Pub. No.: WO2011/124573
PCT Pub. Date: Oct. 13, 2011

(65) Prior Publication Data
US 2013/0084253 A1    Apr. 4, 2013

(30) Foreign Application Priority Data
Apr. 9, 2010    (EP) .................... 10159446

(51) Int. Cl.
*A61K 8/58* (2006.01)
*A61Q 11/00* (2006.01)
*A61K 8/27* (2006.01)
*A61K 8/35* (2006.01)
*A61K 8/365* (2006.01)

(52) U.S. Cl.
CPC ... *A61K 8/58* (2013.01); *A61K 8/27* (2013.01); *A61K 8/35* (2013.01); *A61K 8/365* (2013.01); *A61Q 11/00* (2013.01); *A61K 2800/58* (2013.01)
USPC ............... 424/49; 424/641; 424/756

(58) Field of Classification Search
CPC ...................................... A61K 31/12
USPC ............... 424/9.71, 643, 756; 514/23
See application file for complete search history.

(56) References Cited

U.S. PATENT DOCUMENTS

| | | | |
|---|---|---|---|
| 4,263,333 A * | 4/1981 | Maing et al. .................. 426/540 |
| 6,210,701 B1 * | 4/2001 | Darland et al. ............... 424/439 |
| 6,352,712 B1 | 3/2002 | Lukaczer et al. |
| 2003/0091517 A1 | 5/2003 | Rojanapanthu et al. |
| 2004/0121024 A1 | 6/2004 | Gorsek |
| 2005/0222250 A1 * | 10/2005 | Rezvani ....................... 514/461 |
| 2006/0105064 A1 * | 5/2006 | Berkson et al. ............... 424/756 |
| 2007/0053849 A1 | 3/2007 | Doyle et al. |
| 2007/0196381 A1 | 8/2007 | Holt |
| 2007/0280888 A1 * | 12/2007 | Fujikawa et al. ............ 424/9.71 |
| 2008/0138417 A1 * | 6/2008 | Grigsby ....................... 424/489 |
| 2008/0268095 A1 | 10/2008 | Herzog |
| 2009/0297569 A1 | 12/2009 | Hurwitz |

FOREIGN PATENT DOCUMENTS

| | | |
|---|---|---|
| DE | 202005020103 U1 | 6/2006 |
| GB | 2317339 A | 3/1998 |
| SU | 1132945 | 1/1985 |
| WO | WO2006032666 A1 | 3/2006 |
| WO | WO2007105071 A2 | 9/2007 |
| WO | WO2008042944 A2 | 4/2008 |

OTHER PUBLICATIONS

International Search Report, PCT/EP2011/055278, mailed May 9, 2011, 4 pp.

\* cited by examiner

*Primary Examiner* — Walter Webb
(74) *Attorney, Agent, or Firm* — Greenberg Traurig, LLP

(57) ABSTRACT

The invention provides an oral care composition (preferably a dentifrice) comprising one or more curcumin compounds and a source of zinc ions. The incorporation of a source of zinc ions into the composition suppresses the degradation and/or discoloration of the curcumin compound(s) in the composition.

2 Claims, No Drawings

ORAL CARE COMPOSITIONS

FIELD OF THE INVENTION

The present invention is concerned with oral care compositions. More particularly, the present invention is concerned with oral care compositions containing curcumin compounds.

BACKGROUND OF THE INVENTION

Curcumin compounds have antioxidant properties and may be used in oral care compositions to exert beneficial physiological effects, such as prevention or amelioration of gingivitis or periodontitis. GB 2317339 discloses oral compositions for prevention and treatment of dental caries, periodontal diseases and other diseases of the oral cavity. The compositions include a curcuminoid and a fluoride ion source, in combination with oral care actives and carrier materials. SU 1,132,945 discloses incorporating extracts of turmeric or ginger into toothpaste compositions for improved anti-inflammatory effect on tissues of the oral cavity and treatment of certain diseases of the mucous membranes of the oral cavity and marginal periodontitis.

However, the incorporation of curcumin compounds into oral care compositions (such as toothpastes) presents problems. Degradation and unattractive discoloration have been observed on storage, especially at elevated temperatures.

The present inventors have found that the above problems can be solved by incorporating a source of zinc ions into the composition.

SUMMARY OF THE INVENTION

The present invention provides an oral care composition comprising one or more curcumin compounds and a source of zinc ions.

In another aspect the invention provides the use of a source of zinc ions for suppressing the degradation and/or discoloration of curcumin compound(s) in an oral care composition.

DETAILED DESCRIPTION OF THE INVENTION

Curcumin is a polyphenolic yellow pigment which occurs naturally in the rhizome of the species *Curcuma longa*, which is grown commercially and sold as turmeric, a yellow-orange dye. Curcumin is also known as diferuloylmethane or (1E,6E)-1,7-bis(4-hydroxy-3-methoxy-phenyl)hepta-1,6-diene-3,5-dione. Turmeric contains curcumin along with other natural analogues of curcumin which are collectively called "curcuminoids". The major curcuminoids present in turmeric are demethoxycurcumin (also known as p-hydroxycinnamoyl(feruloyl)methane), bis-demethoxycurcumin (also known as p,p'-dihydroxydicinnamoylmethane) and cyclocurcumin (in which the alpha, beta-unsaturated beta-diketone group of curcumin is replaced by an alpha, beta-unsaturated dihydropyranone group). The term "curcumin compound" for the purposes of the present invention encompasses curcumin, the curcuminoids, other natural or synthetic derivatives or analogues of curcumin, and also preparations of the plant *Curcuma longa* or other curcumin-containing plants, such as *Curcuma xanthorrhiza*, *Curcuma zedoaria* and *Curcuma aromatica*. Examples of typical curcumin compounds for use in the present invention include curcumin, demethoxycurcumin, bis-demethoxycurcumin, sodium and other alkali metal curcuminates, diacetylcurcumin, triethylcurcumin, dihydrocurcumin, tetrahydrocurcumin, tetrahydrodemethoxycurcumin, tetrahydrobis-demethoxycurcumin, hexahydrocurcumin, octahydrocurcumin, curcumin glucuronide, and curcumin sulphate. Preferred examples are curcumin, demethoxycurcumin, bis-demethoxycurcumin, tetrahydrocurcumin, tetrahydrodemethoxycurcumin and tetrahydrobis-demethoxycurcumin. Mixtures of any of the above described materials may also be used. Especially preferred are mixtures of curcumin, demethoxycurcumin and bis-demethoxycurcumin, and most especially mixtures of tetrahydrocurcumin, tetrahydrodemethoxycurcumin and tetrahydrobis-demethoxycurcumin.

The amount of curcumin compound(s) suitably ranges from 0.0001 to 3%, preferably from 0.01 to 2%, more preferably from 0.5 to 1.5% by total weight curcumin compound(s) based on the total weight of the oral care composition.

Suitable sources of zinc ions for use in the present invention include various cosmetically acceptable soluble or sparingly-soluble zinc salts. Sparingly-soluble zinc salts are preferred, since these may further improve product aesthetics by providing an additional opacifying effect. Soluble zinc salts are defined as at least 1 g of zinc salt dissolved per 100 g of solvent at 25° C. Sparingly-soluble zinc salts are defined as from 0.1 to 1 g of zinc salt dissolved per 100 g of solvent at 25° C. Since the compositions of the invention are usually aqueous-based, the "solvent" in the above context is usually water. Specific examples of water-soluble zinc salts which are useful in the present invention include zinc chloride, zinc acetate, zinc gluconate, zinc sulphate and zinc fluoride. Preferably the zinc salt is sparingly water-soluble (for the reason given above), and specific examples of sparingly water-soluble zinc salts which are useful in the present invention include zinc citrate, zinc lactate, zinc oxide, zinc monoglycerolate, zinc tartrate, zinc pyrophosphate and zinc maleate. Zinc citrate is especially preferred since the citrate ion may also contribute to enhanced product stability. Mixtures of any of the above described materials may also be used.

The amount of the source of zinc ions used in the composition of the invention will depend on the particular source used, but suitably ranges from 0.001 to 10% by total weight source of zinc ions based on the total weight of the oral care composition. Zinc citrate is the preferred source of zinc ions for the purposes of the present invention and its amount suitably ranges from 0.001 to 7%, preferably from 0.02 to 2%, more preferably from 1 to 3% by total weight zinc citrate based on the total weight of the oral care composition.

Further antioxidant compounds may usefully be incorporated into compositions of the present invention, in order to boost performance and/or product stability.

A preferred class of such further antioxidant compounds includes tocopherols and derivatives thereof. The tocopherols are mono, di, and trimethylated derivatives of the parent substance tocol (2-methyl-2-(4,8,12-trimethyltridecyl)chroman-6-ol). The configuration 2R,4'R,8'R is assigned to alpha-tocopherol, which occurs most frequently in nature and is the most important source of vitamin E activity. It is occasionally also called RRR-alpha-tocopherol. The tocopherols and derivatives thereof which are preferred for use in the invention are alpha-tocopherol and its esters, such as alpha-tocopherol succinate, alpha-tocopherol nicotinate and alpha-tocopherol acetate. Alpha-tocopherol acetate is especially preferred. Mixtures of any of the above described materials may also be used.

When present, the amount of tocopherols and/or derivatives thereof suitably ranges from 0.0001 to 10%, preferably from 0.01 to 5%, more preferably from 0.5 to 1.5% by total weight tocopherols and/or derivatives thereof based on the total weight of the oral care composition.

Another preferred class of further antioxidant compounds includes alkyl esters of gallic acid. Examples of alkyl esters of gallic acid which are useful in the present invention include n-propyl gallate (n-propyl-3,4,5-trihydroxybenzoate) or isopropyl gallate (isopropyl-3,4,5-trihydroxybenzoate) or gallic acid methyl ester (methyl-3,4,5-trihydroxybenzoate) or gallic acid ethyl ester (ethyl-3,4,5-trihydroxybenzoate)- or gallic acid butyl ester (n-butyl-3,4,5-trihydroxybenzoate). The preferred alkyl ester of gallic acid for the purposes of the present invention is n-propyl gallate. Mixtures of any of the above described materials may also be used.

When present, the amount of alkyl ester of gallic acid suitably ranges from 0.0001 to 3%, preferably from 0.01 to 0.5%, more preferably from 0.01 to 0.05% by total weight alkyl ester of gallic acid based on the total weight of the oral care composition.

Another preferred class of further antioxidant compounds includes ascorbic acid and/or derivatives thereof. The ascorbic acid and/or derivatives thereof for use in the present invention may be ascorbic acid and/or any cosmetically acceptable water-soluble or oil-soluble ascorbic acid derivative. The term "ascorbic acid and/or derivatives thereof" encompasses ascorbic acid as well as esters of ascorbic acid, and ester salts of ascorbic acid such as ascorbyl phosphates as well as ascorbic acid derivatives such as ascorbyl palmitate, ascorbyl tetraisopalmitate (for example available from DSM), ascorbyl dipalmitate (for example, NIKKOL CP available from Nikko Chemical), ascorbyl linoleate, ascorbyl octanoate, 2-O-D-glucopyranosyl-L-ascorbic acid, which is an ester of ascorbic acid and glucose and usually referred to as L-ascorbic acid 2-glucoside or ascorbyl glucoside, and its metal salts. The term "ascorbyl phosphate" denotes metal salts of mono- and polyphosphoric acid esters of ascorbic acid in which the phosphorylated hydroxy group of the ascorbic acid molecule features one or more phosphoric acid (phosphate) units, and in which metal cations (such as sodium and/or magnesium or calcium ions) are also present. The term "poly" generally denotes 2 to 10, preferably 2 to 4 phosphate units. The ascorbyl phosphates may also be referred to in general as "ascorbyl (poly)phosphates" to embrace both mono- and polyphosphates. Typical ascorbyl phosphates for use in the present invention are L-ascorbic acid phosphate ester salts such as sodium ascorbyl phosphate, potassium ascorbyl phosphate, magnesium ascorbyl phosphate, calcium ascorbyl phosphate and sodium magnesium L-ascorbyl-2-monophosphate. Commercially available ascorbyl phosphates comprise trisodium L-ascorbyl-2-monophosphate which is available as STAY-C®50 form DSM Nutritional Products AG, (4303 Kaiseraugst, Switzerland) and magnesium L-ascorbyl phosphate (available from Showa Denko) and sodium magnesium L-ascorbyl-2-monophosphate. The preferred ascorbyl phosphate for the purposes of the present invention is trisodium L-ascorbyl-2-monophosphate. Mixtures of any of the above described materials may also be used.

When present, the amount of ascorbic acid and/or derivatives thereof suitably ranges from 0.0001 to 10%, preferably from 0.01 to 5%, more preferably from 1 to 3% by total weight ascorbic acid and/or derivatives thereof based on the total weight of the oral care composition.

Mixtures of any of the above described further antioxidant compounds may also be used. Particularly preferred are mixtures including at least two of, and most preferably all of, the following further antioxidant compounds: alpha-tocopherol acetate, n-propyl gallate and ascorbyl phosphate (in suitable individual amounts such as those specified above according to the class of antioxidant).

The total amount of further antioxidant compound(s) suitably ranges from 0.0001 to 15%, preferably from 0.01 to 5%, more preferably from 2 to 4% by total weight further antioxidant compound(s) based on the total weight of the oral care composition.

The oral care compositions of the invention may be in any form common in the art, for example a dentifrice, a mouthwash, gum or lozenge.

A preferred type of product form in the context of the present invention is a dentifrice. The term "dentifrice" denotes paste, cream, mousse, aerosol, powder, gel, and/or liquid formulations which are used to clean the surfaces of the oral cavity. The dentifrice is an oral composition that is not intentionally swallowed for purposes of systemic administration of therapeutic agents, but is retained in the oral cavity for a sufficient time to contact substantially all of the dental surfaces and/or mucosal tissues for purposes of oral activity. Preferably the dentifrice is in the form of a paste or a gel (or a combination thereof).

A dentifrice composition according to the invention will generally contain further ingredients to enhance performance and/or consumer acceptability such as abrasive cleaning agent, water, humectant, binder or thickening agent, and surfactant.

For example, a dentifrice will usually comprise an abrasive cleaning agent in an amount of from 3 to 75% by weight based on the total weight of the dentifrice. Suitable abrasive cleaning agents include silica xerogels, hydrogels and aerogels and precipitated particulate silicas; calcium carbonate, dicalcium phosphate, tricalcium phosphate, calcined alumina, sodium and potassium metaphosphate, sodium and potassium pyrophosphates, sodium trimetaphosphate, sodium hexametaphosphate, particulate hydroxyapatite and mixtures thereof.

Furthermore, the dentifrice will usually contain a liquid phase in an amount of from 40 to 99% by weight based on the total weight of the dentifrice. Such a liquid phase typically comprises water and a humectant in various relative amounts, with the amount of water generally ranging from 10 to 45% by weight (based on the total weight of the dentifrice) and the amount of humectant generally ranging from 30 to 70% by weight (based on the total weight of the dentifrice). Typical humectants include glycerol, sorbitol, polyethylene glycol, polypropylene glycol, propylene glycol, xylitol (and other edible polyhydric alcohols), hydrogenated partially hydrolyzed polysaccharides and mixtures thereof.

Furthermore, the dentifrice will usually contain a binder or thickening agent in an amount of from 0.5 to 10% by weight based on the total weight of the dentifrice. Suitable binders or thickening agents include carboxyvinyl polymers (such as polyacrylic acids cross-linked with polyallyl sucrose or polyallyl pentaerythritol), hydroxyethyl cellulose, hydroxypropyl cellulose, water soluble salts of cellulose ethers (such as sodium carboxymethyl cellulose and sodium carboxymethyl hydroxyethyl cellulose), natural gums (such as carrageenan, gum karaya, guar gum, xanthan gum, gum arabic, and gum tragacanth), finely divided silicas, hectorites, colloidal magnesium aluminium silicates and mixtures thereof.

Furthermore, the dentifrice will usually contain a surfactant in an amount of from 0.2 to 5% by weight based on the total weight of the dentifrice. Suitable surfactants include anionic surfactants, such as the sodium, magnesium, ammonium or ethanolamine salts of $C_8$ to $C_{18}$ alkyl sulphates (for example sodium lauryl sulphate), $C_8$ to $C_{18}$ alkyl sulphosuccinates (for example dioctyl sodium sulphosuccinate), $C_8$ to $C_{18}$ alkyl sulphoacetates (such as sodium lauryl sulphoacetate), $C_8$ to $C_{18}$ alkyl sarcosinates (such as sodium lauryl sarcosinate), $C_8$ to $C_{18}$ alkyl phosphates (which can optionally comprise up to 10 ethylene oxide and/or propylene oxide units) and sulphated monoglycerides. Other suitable surfactants include nonionic surfactants, such as optionally polyethoxylated fatty acid sorbitan esters, ethoxylated fatty acids, esters of polyethylene glycol, ethoxylates of fatty acid monoglycerides and diglycerides, and ethylene oxide/propylene oxide block polymers. Other suitable surfactants include amphoteric surfactants, such as betaines or sulphobetaines. Mixtures of any of the above described materials may also be used.

Compositions of the present invention may also contain further optional ingredients customary in the art such as fluoride ion sources, anticalculus agents, buffers, flavouring agents, sweetening agents, colouring agents; opacifying agents, preservatives, antisensitivity agents and antimicrobial agents.

The invention is further illustrated with reference to the following, non-limiting Examples.

EXAMPLES

Compositions were prepared having ingredients as shown in Table 1 below.

All ingredients are expressed by weight percent of the total formulation, and as level of active ingredient.

Example A is a comparative example (not according to the invention). Example 1 is a formulation according to the invention.

TABLE 1

| Ingredient | Example 1 | Example A |
|---|---|---|
| Sorbitol | 45 | 45 |
| Sodium fluoride | 0.32 | 0.32 |
| Sodium saccharin | 0.25 | 0.25 |
| PEG-32 | 2.0 | 2.0 |
| Zinc citrate | 2.0 | — |
| Titanium dioxide | 1.0 | 1.0 |
| Hydrated silica (Tixosil ®43, ex Rhodia) | 8.5 | 8.5 |
| Hydrated silica (Sorbosil ®AC77, ex PQ Corp.) | 10 | 10 |
| Sodium lauryl sulphate | 1.8 | 1.8 |
| Flavour | 1.2 | 1.2 |
| Carboxymethylcellulose, sodium salt (Cekol ® 2000, ex CP Kelco) | 1.1 | 1.1 |
| THC(TETRAHYDROCURCUMINOIDS CG, ex Sabinsa Corp.)* | 1.0 | 1.0 |
| Propyl gallate | 0.03 | 0.03 |
| Tocopheryl acetate | 1.0 | 1.0 |
| Sodium ascorbyl phosphate (Stay-C ® 50, ex DSM) | 2.0 | 2.0 |
| Water | to 100 | To 100 |

*A mixture of tetrahydrocurcumin, tetrahydrodemethoxycurcumin and tetrahydrobisdemethoxycurcumin extracted from the roots of the *Curcuma longa* (turmeric) plant.

After 4 months storage at elevated temperature (40° C.), the formulations were tested for THC levels. The percentage of THC recovered from the formulation of Example 1 was 91%. By contrast, the percentage of THC recovered from the formulation of Example A was 64%, indicating greater THC degradation in the formulation of Example A.

The invention claimed is:

1. A composition comprising:
   a sufficient amount of the following components to form a first oral care composition:
   one or more curcumin compounds;
   zinc citrate;
   a dentifrice ingredient; and
   at least one tocopherol or tocopherol derivative;
   wherein the dentifrice ingredient is an abrasive cleaning agent;
   wherein the first oral care composition comprises a sufficient amount of the zinc citrate such that, when the first oral care composition is stored for four months at a temperature of 40 degrees Celsius, a degradation of the one or more curcumin compounds is reduced 75% compared with a second oral care composition;
   and wherein the second oral care composition is identical to the first oral care composition except the second oral care composition does not include zinc citrate.

2. An oral care composition according to claim 1, in which the curcumin compound is a mixture of tetrahydrocurcumin, tetrahydrodemethoxycurcumin and tetrahydrobisdemethoxycurcumin.

* * * * *